(12) United States Patent
Cheng

(10) Patent No.: US 11,369,406 B2
(45) Date of Patent: Jun. 28, 2022

(54) MEDICAL DEVICE

(71) Applicant: Gyrus ACMI, Inc., Southborough, MA (US)

(72) Inventor: Ming Cheng, W. Warwick, RI (US)

(73) Assignee: Gyrus Acmi, Inc., Westborough, MA (US)

( * ) Notice: Subject to any disclaimer, the term of this patent is extended or adjusted under 35 U.S.C. 154(b) by 150 days.

(21) Appl. No.: 15/907,771

(22) Filed: Feb. 28, 2018

(65) Prior Publication Data
US 2019/0262025 A1 Aug. 29, 2019

(51) Int. Cl.
*A61B 17/3205* (2006.01)

(52) U.S. Cl.
CPC .............................. *A61B 17/32053* (2013.01)

(58) Field of Classification Search
CPC ........ A61B 17/32053; A61B 17/32002; A61B 2017/32004; A61B 2017/00407; A61B 2217/007; A61B 2217/005; A61B 2017/2837; A61B 2017/00845; A61B 2017/320032; A61B 17/2833
See application file for complete search history.

(56) References Cited

U.S. PATENT DOCUMENTS

| | | | | |
|---|---|---|---|---|
| 3,995,619 | A | * 12/1976 | Glatzer | A61B 10/0275 600/550 |
| 4,621,639 | A | * 11/1986 | Transue | A61B 17/04 606/215 |
| 4,909,789 | A | * 3/1990 | Taguchi | A61B 17/0218 604/107 |
| 4,932,394 | A | * 6/1990 | Nanaumi | A61B 1/00055 600/148 |
| 5,320,110 | A | * 6/1994 | Wang | A61B 10/0275 600/566 |
| 7,462,187 | B2 | 12/2008 | Johnston et al. | |
| 8,419,720 | B1 | * 4/2013 | Dawoodjee | A61B 17/29 606/1 |
| 9,486,232 | B2 | 11/2016 | Heisler et al. | |
| 10,299,819 | B2 | * 5/2019 | Akilian | A61B 17/32002 |
| 2009/0112119 | A1 | * 4/2009 | Kim | A61B 10/0275 600/564 |

(Continued)

FOREIGN PATENT DOCUMENTS

WO 2010/104850 A1 9/2010

OTHER PUBLICATIONS

"Multidebrider Diego Elite". Retrieved Feb. 28, 2018, from http://medical.olympusamerica.com/products/debrider/diego%C2%AE-elite, 2 pages.

*Primary Examiner* — Jocelin C Tanner
(74) *Attorney, Agent, or Firm* — Schwegman Lundberg & Woessner, P.A.

(57) ABSTRACT

Disclosed herein is a medical device. The medical device includes an outer tubular member, an inner tubular member, and a lock pin. The outer tubular member has a proximal end, a distal end, and an open window disposed at the distal end. The inner tubular member has a proximal end, a distal end, and an open window disposed at the distal end. The inner tubular member is configured to be received within the outer tubular member and capable of rotating and/or translating relative to the outer tubular member. The lock pin is configured to set the open window of the outer tubular member at a pre-determined orientation.

19 Claims, 7 Drawing Sheets

(56) References Cited

U.S. PATENT DOCUMENTS

| | | | | |
|---|---|---|---|---|
| 2012/0065658 A1* | 3/2012 | Heisler | ............ | A61B 17/32002 606/170 |
| 2012/0130275 A1* | 5/2012 | Chudzik | ............ | A61B 10/0283 600/567 |
| 2012/0172889 A1* | 7/2012 | Chin | ................ | A61B 17/32002 606/119 |
| 2013/0030456 A1* | 1/2013 | Assell | ................ | A61B 17/1617 606/170 |
| 2014/0277036 A1* | 9/2014 | Flynn | ................ | A61B 17/3205 606/170 |
| 2018/0242962 A1* | 8/2018 | Walen | ................ | A61B 17/1659 |
| 2019/0083121 A1* | 3/2019 | Benamou | ............ | A61B 17/1615 |
| 2019/0099195 A1* | 4/2019 | Carroll | ............. | A61B 17/32002 |

\* cited by examiner

MEDICAL DEVICE

BACKGROUND

Field of the Invention

The invention relates to a medical device and more specifically relates to alignment features for a medical device.

Brief Description of Prior Developments

Conventional medical devices having cutting blades and tools comprise complicated configurations which can lead to more failures, provide a challenge to manufacturing, and added cost. Accordingly, there is a need to provide improved and reliable medical device configurations.

SUMMARY

In accordance with one aspect of the invention, a medical device is disclosed. The medical device includes an outer tubular member, an inner tubular member, and a lock pin. The outer tubular member has a proximal end, a distal end, and an open window disposed at the distal end. The inner tubular member has a proximal end, a distal end, and an open window disposed at the distal end. The inner tubular member is configured to be received within the outer tubular member and capable of rotating and/or translating relative to the outer tubular member. The lock pin is configured to set the open window of the outer tubular member at a predetermined orientation.

In accordance with another aspect of the invention, a medical device is disclosed. The medical device includes an outer tubular member, an inner tubular member, and an alignment knob. The outer tubular member has a proximal end, a distal end, and an open window disposed at the distal end. The inner tubular member has a proximal end, a distal end, and an open window disposed at the distal end. The inner tubular member is configured to be received within the outer tubular member and capable of rotating and/or translating relative to the outer tubular member. The alignment knob is configured to align the open window of the outer tubular member with the open window of the inner tubular member.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
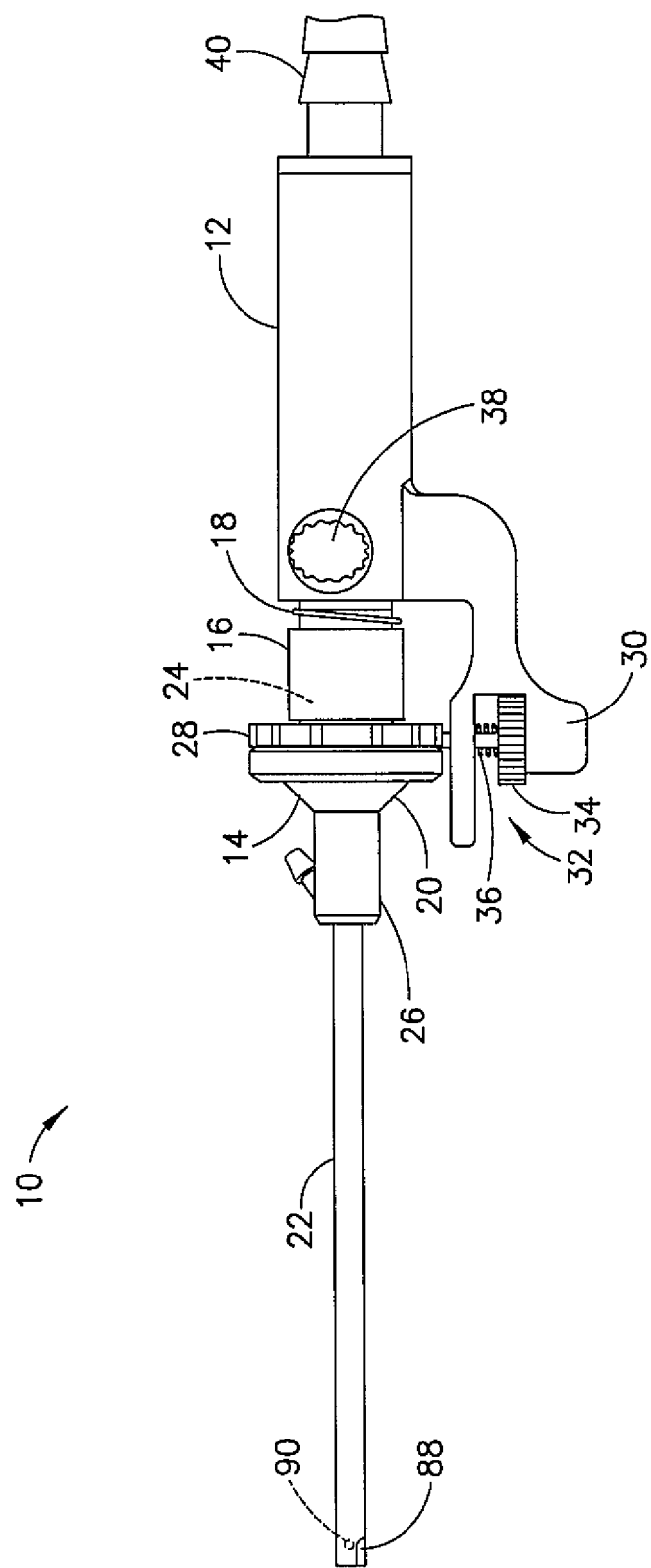
FIG. 1 is a side view of a medical device incorporating features of the invention.
Figure 2:
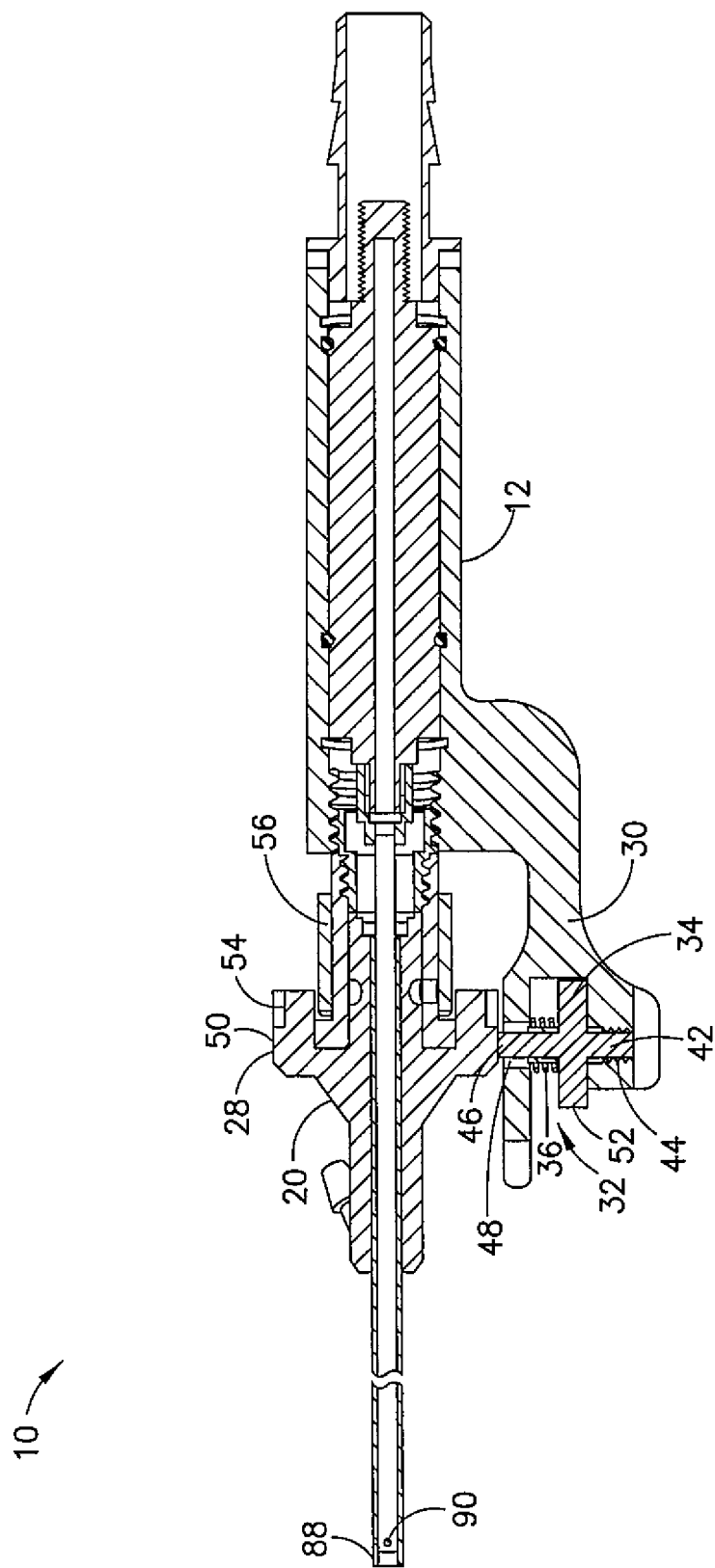
FIG. 2 is a section view of the medical device shown in FIG. 1.
Figure 3:
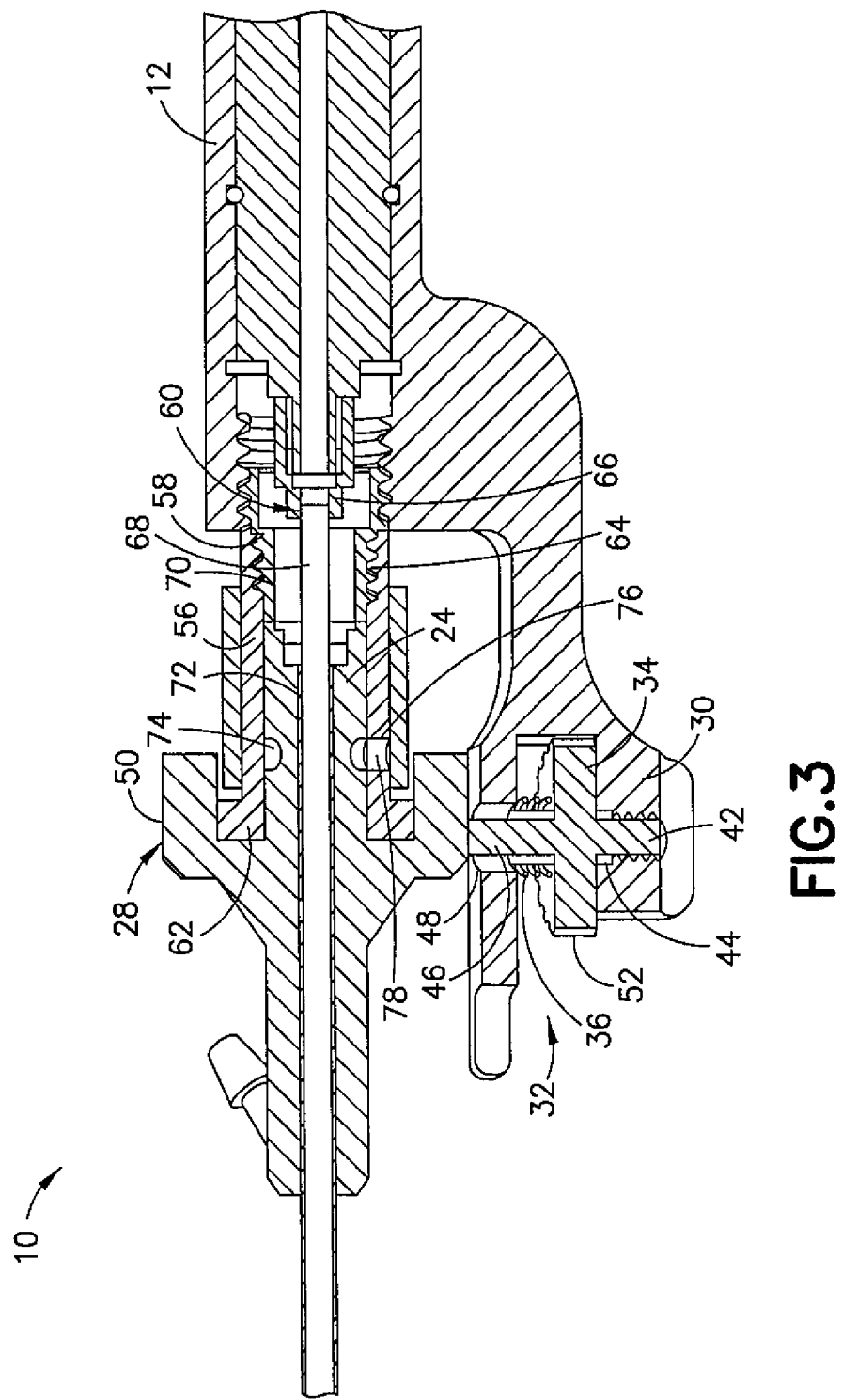
FIG. 3 is an enlarged section view of the medical device shown in FIG. 1.
Figure 4:
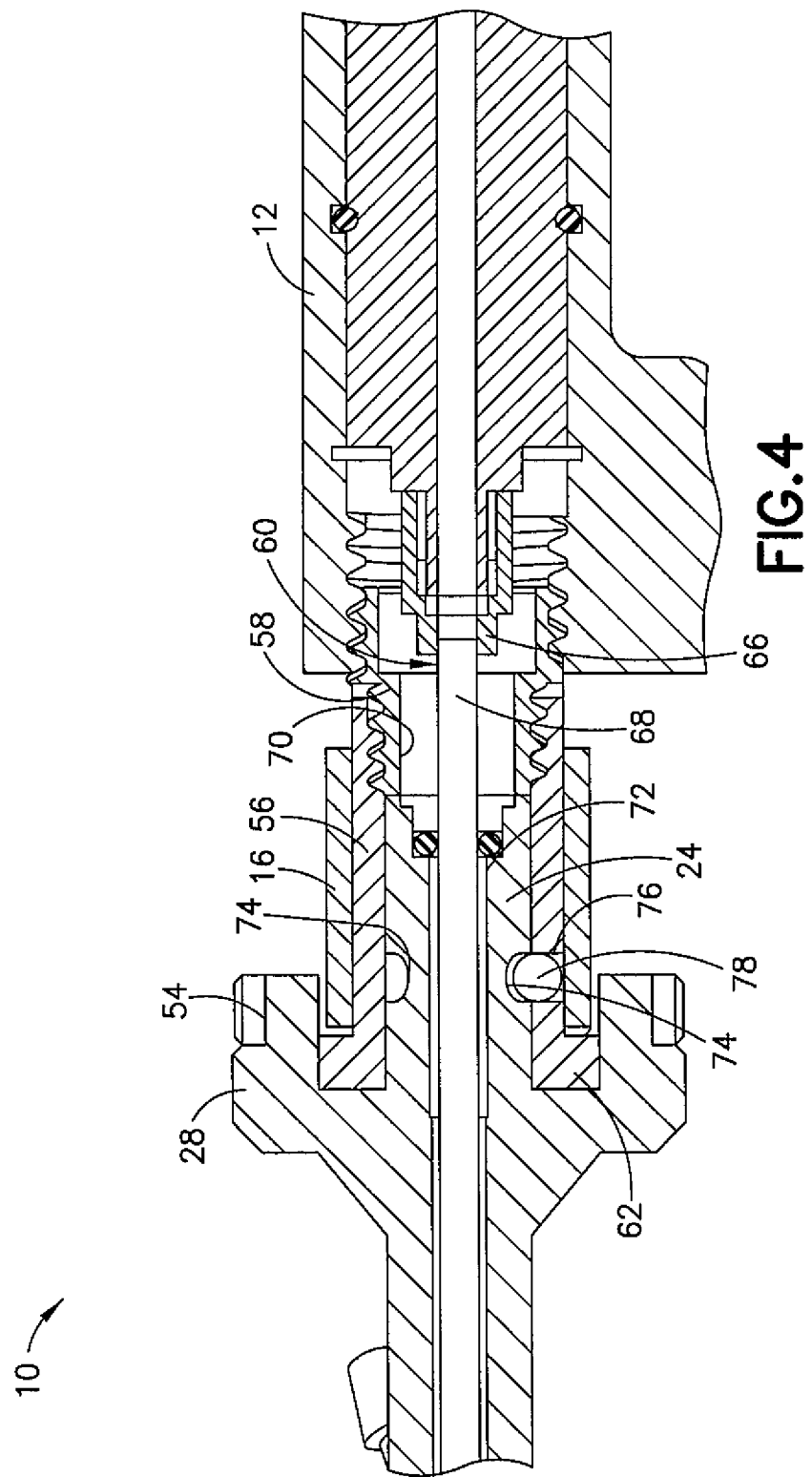
FIG. 4 is another enlarged section view of the medical device shown in FIG. 1.
Figure 5:
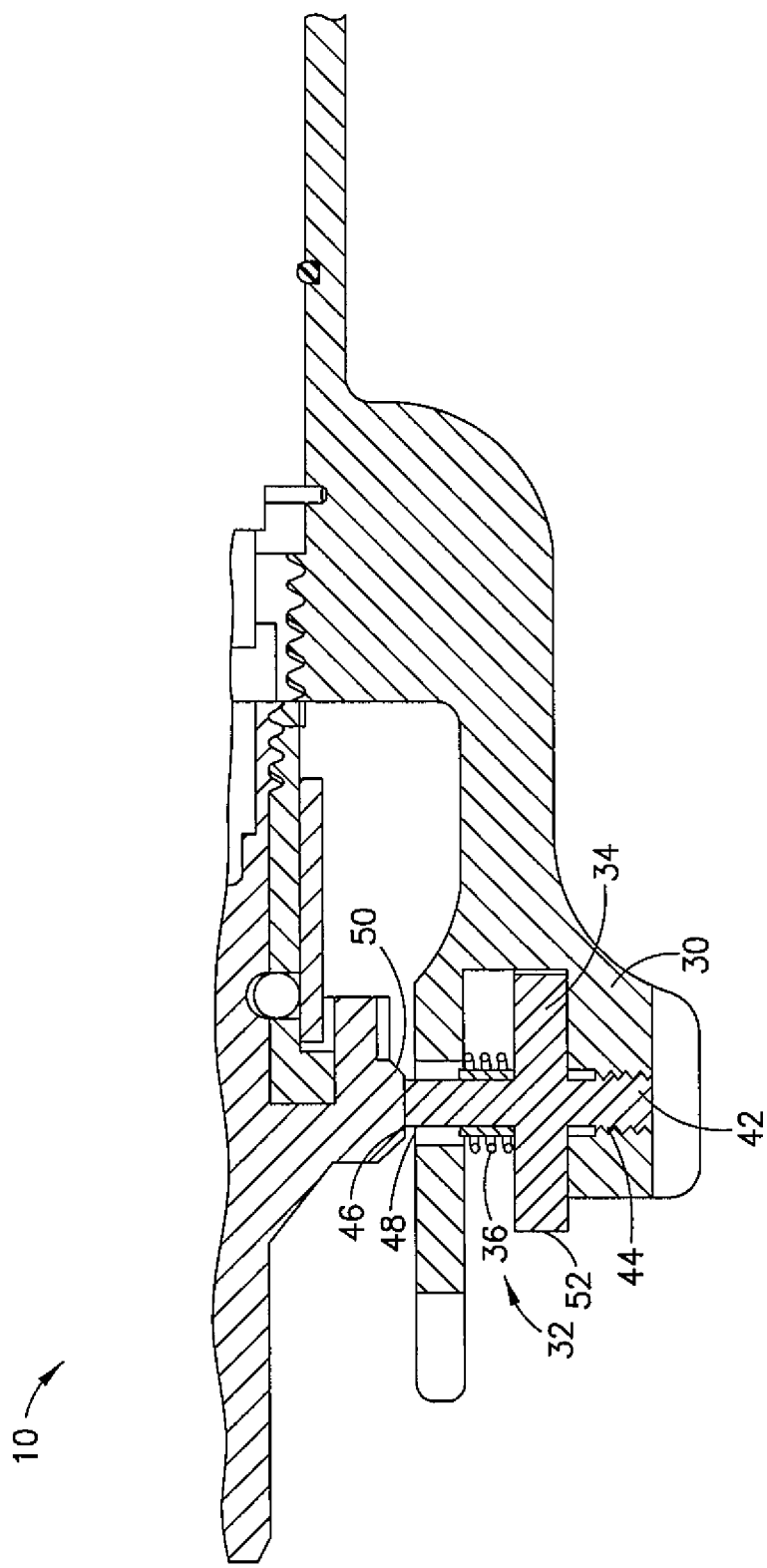
FIG. 5 is another enlarged section view of the medical device shown in FIG. 1.

Referring to FIG. 1, there is shown a side view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is a high speed cutting tool or instrument. Additionally, the medical device 10 may be an ENT debrider, a microdebrider, an ENT instrument, or any other suitable medical device comprising cutting blades and/or tools.

The medical device 10 comprises a handpiece housing 12, an outer blade assembly 14, and an outer cylindrical member 16. The outer cylindrical member 16 is between the handpiece housing 12 and the outer blade assembly 14. Additionally, a spring 18 may be provided between the outer cylindrical member 16 and the handpiece housing 12.

The outer blade assembly 14 comprises an outer blade housing 20 and an outer blade 22. The outer blade housing 20 comprises a proximal barrel section 24, a distal barrel section 26, and a ring section 28 between the proximal barrel section 24 and the distal barrel section 26.

The handpiece housing 12 further comprises an extension portion 30 which extends adjacent the outer cylindrical member 16 and the ring section 28. The extension portion 30 comprises a slotted section 32 configured to accommodate an outer blade lock pin 34 and a spring 36.

The medical device 10 also comprises an alignment knob 38 at a distal end of the housing 12 and a suction and/or irrigation connection 40 for a tube (not shown) at a proximal end of the handpiece housing 12.

Referring now also to FIGS. 2-5, there are shown various section views of the medical device 10. The outer blade lock pin 34 and the spring 36 are received within the slotted section 32 such that a threaded portion 42 of the pin 34 engages with a threaded hole 44 of the extension portion 30 and a contact section 46 of the pin 34 extends through an opening 48 of the extension portion 30 and contacts on outer periphery 50 of the ring section 28 of the outer blade housing 20. According to some exemplary embodiments, the periphery 50 of the outer blade housing 20 may comprises a notched (or grooved) pattern 54 configured to promote engagement of the contact section 46 with the outer periphery 50. With this configuration, a rotation of a central portion 52 of the pin 34 in a first direction moves the contact section 46 towards the periphery 50 of the outer blade housing 20, and a rotation of the central portion 52 of the pin in a second opposite direction moves the contact section 46 away from the periphery 50 of the outer blade housing 20.

The medical device 10 further comprises an inner cylindrical member 56, a threaded connecting member 58, and an inner blade assembly 60. The inner cylindrical member 56 comprises a tubular shape with a flange 62 at a distal end and a threaded portion 64 at a proximal end. The inner cylindrical member 56 is between the proximal barrel 24 and the outer cylindrical member 16. The inner blade assembly 60 comprises a base section and an inner blade 68. The base section 66 is connected to the housing 12 and the inner blade 68 extends through a central opening 70 of the connecting member 58 and a central opening 72 of the outer blade housing 16.

The proximal barrel 24 comprises one or more openings (or grooves) 74 and the inner cylindrical member comprises corresponding one or more openings (or grooves) 76. A lock ball 78 or other similar locking member (such as a quick connect/release mechanism between a ratchet drive and socket, for example) is provided between the proximal barrel 24 and the inner cylindrical member 56 so that the locking member 78 engages the one or more openings (or grooves) 74 and the one or more openings (or grooves) 76.

Figure 6:
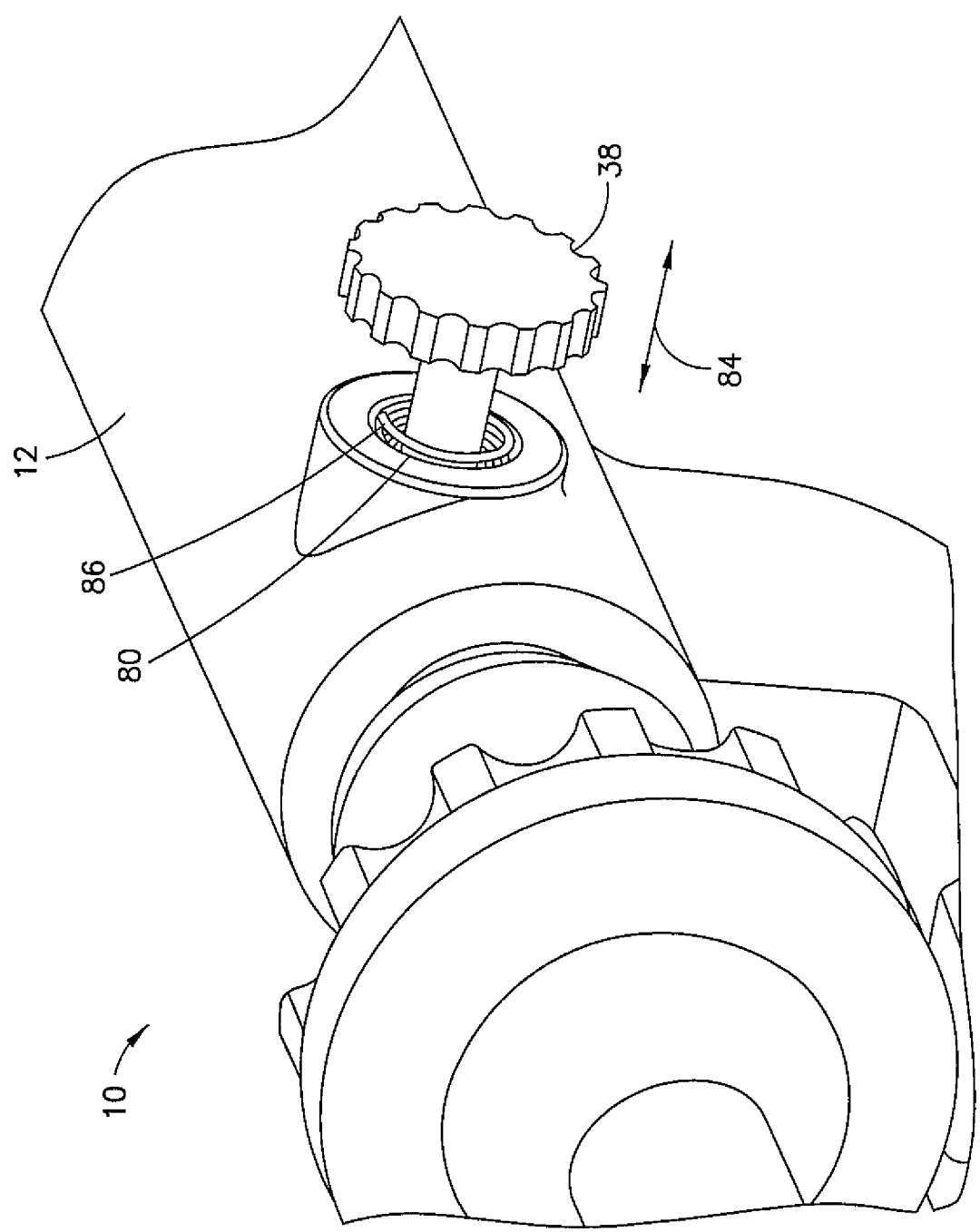
FIG. 6 is a perspective view of the medical device shown in FIG. 1.
Figure 7:
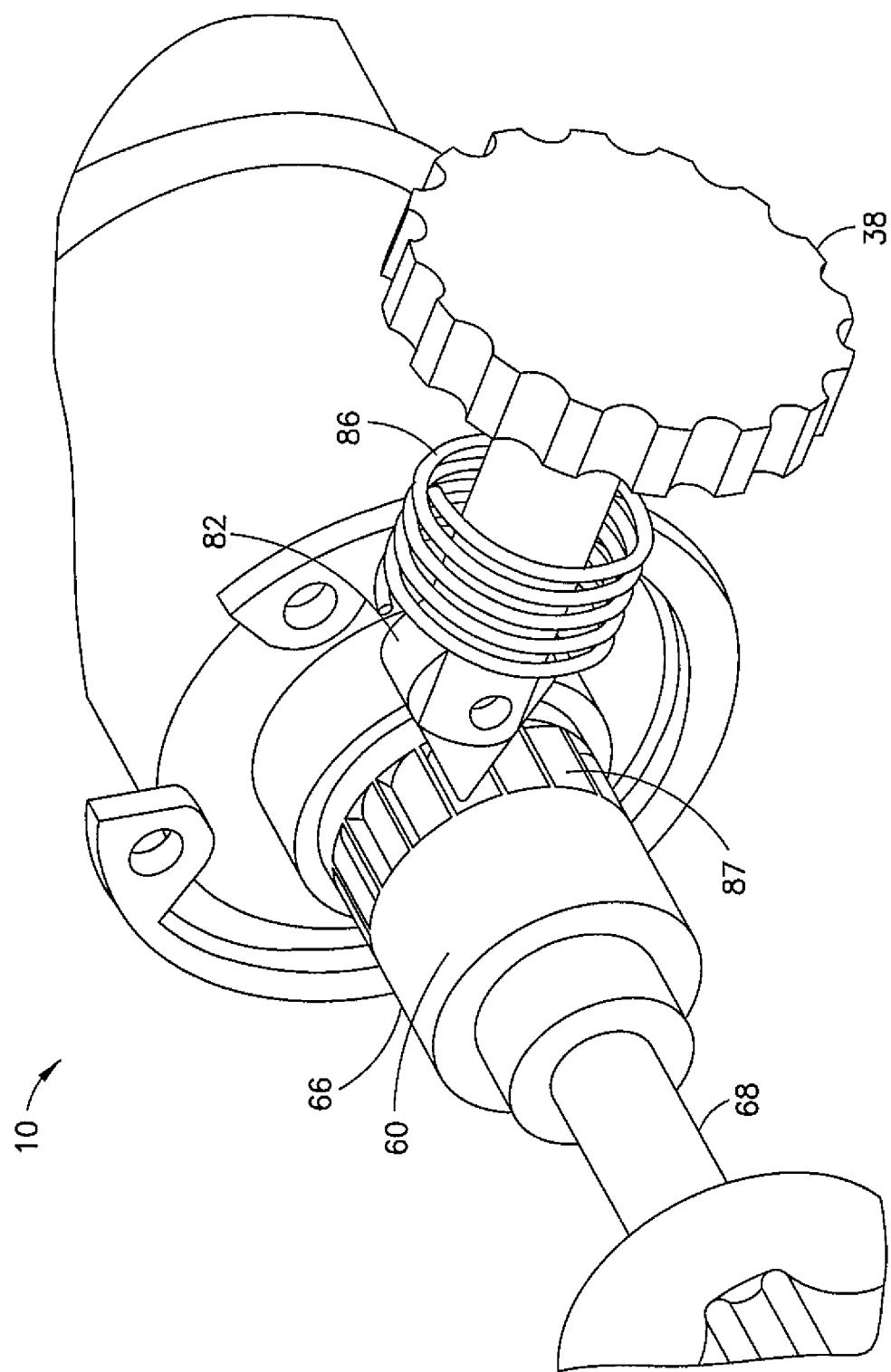
FIG. 7 is a perspective view of internal portions of the medical device shown in FIG. 1.

Referring now also to FIGS. 6 and 7, the alignment knob 38 extends through an opening 80 of the housing 12. A pawl 82 is rotatably connected at an end of the knob 38. The knob 38 may be a push knob configured to move (see arrow 84) within the opening 80, and may further be biased by spring 86. Movement of the knob 38 allows for the pawl 82 to engage a ratchet feature 87 of the inner blade assembly 60. For example, according to various exemplary embodiments, the ratchet feature may be formed integrally with the base section 66. However, in alternate embodiments any suitable ratchet configuration may be provided. Additionally, it should 000 be noted that the pawl 82 may comprise any suitable pivoted curved bar or lever whose free end engages with the ratchet so that the ratchet feature can only turn or move one way (or direction).

The outer blade (or outer blade tube) 22 is mounted to the distal barrel 26 of the outer blade housing 20 and acts as a static member, wherein the inner blade (or inner blade tube) 68 is slidably mounted inside the outer blade 22. When the device 10 is energized, the inner blade 68 is forced distally and/or proximally such that an open window 88 of the outer blade 22 and an open window 90 of the inner blade 68 form a cutting tool when the inner blade translates (and/or rotates) relative to the outer blade (i.e. such as during a surgical operation).

According to various exemplary embodiments, the outer blade and the inner blade each comprise an open window (88, 90 respectively) at a distal end of the device 10. However, in some alternate embodiments only the outer blade comprises an open window.

Various exemplary embodiments of the invention provide for a quick connection mechanism for outer blade axial control. For example, this is provided by the cooperation of the one or more openings (or grooves) 74 of the proximal barrel 24, the one or more openings (or grooves) 76 of the inner cylindrical member 56, and the locking member 76. This provides an axial lock feature for the outer blade which is simple, robust in design and cheap in cost.

Various exemplary embodiments of the invention also provide for a simple screw to lock the outer blade radial orientation (i.e. 0-360° around a central axis of the device). For example, this is provided by the cooperation of the outer blade lock pin 34 with the outer periphery of the ring section 28 in that rotation of the pin 34 allows the end of the pin to engage the outer periphery of the ring section 28 and lock the position (0-360° around the central axis of the device based on rotation of the outer blade assembly)) of the outer blade.

Various exemplary embodiments of the invention also provide for a ratchet mechanism to align the inner blade window with outer blade window. For example, this is provided by the cooperation of the alignment knob 38 and pawl 82 with the ratchet feature 86 to lock the position (0-360° around the central axis of the device based on rotation of the inner blade assembly)) of the inner blade.

Technical effects of any one or more of the exemplary embodiments provide significant advantages over conventional configurations by providing less complicated blade assembly locking systems, outer blade orientation locking mechanisms, and inner blade alignment to outer blade systems. For example, conventional configurations require difficult to use lock tab/lock ring configurations, multiple location sensors, and an electrical assistant. Whereas any one or more of the exemplary embodiments provide simplified designs for quick and easy operation which are robust and without added cost.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: an outer tubular member having a proximal end, a distal end, and an open window disposed at the distal end; an inner tubular member having a proximal end, a distal end, and an open window disposed at the distal end, the inner tubular member configured to be received within the outer tubular member and capable of rotating and/or translating relative to the outer tubular member; and a lock pin configured to set the open window of the outer tubular member at a pre-determined orientation.

A medical device as above, wherein the lock pin is accessible from an exterior of the medical device.

A medical device as above, further comprising an alignment knob configured to align the open window of the outer tubular member with the open window of the inner tubular member.

A medical device as above, wherein the alignment knob is accessible from an exterior of the medical device.

A medical device as above, wherein the alignment knob is connected to a pawl.

A medical device as above, wherein the pawl is configured to contact a ratchet feature.

A medical device as above, further comprising an axial lock feature for the outer tubular member.

A medical device as above, wherein the open window of the outer tubular member and the open window of the inner tubular member are configured to form a cutting tool when the inner tubular member rotates and/or translates relative to the outer tubular member during a surgical operation.

A medical device as above, further comprising an outer blade housing, wherein the outer blade is connected to the outer blade housing, and wherein the lock pin is configured to contact the outer blade housing.

In another exemplary embodiment, a medical device comprising: an outer tubular member having a proximal end, a distal end, and an open window disposed at the distal end; an inner tubular member having a proximal end, a distal end, and an open window disposed at the distal end, the inner tubular member configured to be received within the outer tubular member and capable of rotating and/or translating relative to the outer tubular member; and an alignment knob configured to align the open window of the outer tubular member with the open window of the inner tubular member.

A medical device as above, wherein the alignment knob is accessible from an exterior of the medical device.

A medical device as above, further comprising a lock pin configured to set the open window of the outer tubular member at a pre-determined orientation.

A medical device as above, the lock pin is accessible from an exterior of the medical device.

A medical device as above, further comprising an outer blade housing, wherein the outer blade is connected to the outer blade housing, and wherein the lock pin is configured to contact the outer blade housing.

A medical device as above, the alignment knob is connected to a pawl.

A medical device as above, wherein the pawl is configured to contact a ratchet feature.

A medical device as above, further comprising an axial lock feature for the outer tubular member.

A medical device as above, wherein the open window of the outer tubular member and the open window of the inner tubular member are configured to form a cutting tool when the inner tubular member rotates and/or translates relative to the outer tubular member during a surgical operation.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
    an outer tubular member extending along a central longitudinal axis and having a proximal end, a distal end, and an open window disposed at the distal end, the outer tubular member rotatable about the central longitudinal axis to adjust a radial orientation of the open window;
    an inner tubular member having a proximal end, a distal end, and an open window disposed at the distal end, the inner tubular member configured to be received within the outer tubular member and capable of at least one of rotating or translating relative to the outer tubular member;
    a lock pin configured to set the radial orientation of the open window of the outer tubular member at a desired position, wherein the lock pin is accessible from an exterior of the medical device and the outer tubular member is rotatable relative to the lock pin; and
    an alignment knob configured to align the open window of the inner tubular member with the open window of the outer tubular member, the alignment knob being spring-biased and configured to move radially relative to the inner tubular member to release or lock the open window of the inner tubular member with the open window of the outer tubular member.

2. The medical device of claim 1 wherein the alignment knob is accessible from an exterior of the medical device.

3. The medical device of claim 1 wherein the alignment knob is connected to a pawl.

4. The medical device of claim 3 wherein the pawl is configured to contact a ratchet feature.

5. The medical device of claim 1 further comprising an axial lock feature for the outer tubular member.

6. The medical device of claim 1 wherein the open window of the outer tubular member and the open window of the inner tubular member are configured to form a cutting tool when the inner tubular member at least one of rotates or translates relative to the outer tubular member during a surgical operation.

7. The medical device of claim 1 further comprising an outer blade housing, wherein an outer blade is connected to the outer blade housing, and wherein the lock pin is configured to contact the outer blade housing.

8. The medical device of claim 1 wherein the lock pin comprises a spring-biased lock pin.

9. The medical device of claim 1 wherein the outer tubular member is coupled to a ring member including a plurality of notches, and wherein the lock pin is configured to engage one of the notches to set the radial orientation of the open window of the outer tubular member at the desired position.

10. The medical device of claim 9 wherein rotation of the lock pin in a first direction moves a contact portion of the lock pin towards the ring member, and wherein rotation of the lock pin in a second direction moves the contact portion of the lock pin away from the ring member.

11. A medical device of claim 1:
    wherein the open window of the outer tubular member and the open window of the inner tubular member form a cutting tool when the inner tubular member moves relative to the outer tubular member.

12. A medical device comprising:
    a handpiece housing;
    an outer tubular member extending along a central longitudinal axis and having a proximal end, a distal end, and an open window disposed at the distal end, the outer tubular member rotatable about the central longitudinal axis to adjust a radial orientation of the open window;
    an inner tubular member having a proximal end, a distal end, and an open window disposed at the distal end, the inner tubular member configured to be received within the outer tubular member and capable of at least one of rotating or translating relative to the outer tubular member;
    a spring-biased lock pin including a threaded shaft engaged with a threaded aperture in the handpiece housing, the outer tubular member being rotatable relative to the lock pin, and the lock pin configured to set the radial orientation of the open window of the outer tubular member at a desired position, wherein rotation of the lock pin in a first direction moves a contact surface of the lock pin towards the outer tubular member and rotation of the lock pin in a second opposite direction moves the contact surface away from the outer tubular member;
    a spring-biased alignment knob configured to align the open window of the inner tubular member with the open window of the outer tubular member, the alignment knob configured to move radially relative to the inner tubular member to release or lock the open window of the inner tubular member with the open window of the outer tubular member; and
    a coupler member including a locking element;
    wherein the outer tubular member is a component of an outer blade assembly; and
    wherein the coupler member is configured to releasably couple the outer blade assembly to the handpiece housing.

13. The medical device of claim 12 wherein the alignment knob is accessible from an exterior of the medical device.

14. The medical device of claim 12 wherein the lock pin is accessible from an exterior of the medical device.

15. The medical device of claim 12 further comprising an outer blade housing, wherein an outer blade is connected to the outer blade housing, and wherein the lock pin is configured to contact the outer blade housing.

16. The medical device of claim 12 wherein the alignment knob is connected to a pawl.

17. The medical device of claim 16 wherein the pawl is configured to contact a ratchet feature.

18. The medical device of claim 12 further comprising an axial lock feature for the outer tubular member.

19. The medical device of claim 12 wherein the open window of the outer tubular member and the open window of the inner tubular member are configured to form a cutting tool when the inner tubular member at least one of rotates or translates relative to the outer tubular member during a surgical operation.

* * * * *